United States Patent
Smith

(10) Patent No.: US 6,392,546 B1
(45) Date of Patent: May 21, 2002

(54) HAND WASHING COMPLIANCE MEASUREMENT AND RECORDING SYSTEM

(76) Inventor: Judson L. Smith, 1909 E. Rhea Rd., Tempe, AZ (US) 85284

( * ) Notice: Subject to any disclaimer, the term of this patent is extended or adjusted under 35 U.S.C. 154(b) by 0 days.

(21) Appl. No.: 09/657,112

(22) Filed: Sep. 7, 2000

(51) Int. Cl.[7] .............................................. G08B 23/00
(52) U.S. Cl. .............................. 340/573.1; 340/691.1; 222/52; 222/105; 222/185; 222/189
(58) Field of Search ......................... 340/573.1, 691.1; 222/52, 105, 211, 189, 185, 39; 137/552.7, 624.11

(56) References Cited

U.S. PATENT DOCUMENTS

| | | | |
|---|---|---|---|
| 3,878,973 A | 4/1975 | Riccio | 222/319 |
| 4,121,736 A | 10/1978 | McGaw, Jr. | 222/94 |
| 4,212,758 A | 7/1980 | Shashkina et al. | 252/119 |
| 4,219,367 A | 8/1980 | Cary, Jr. et al. | 134/29 |
| 4,238,056 A | 12/1980 | Tucker et al. | 222/181 |
| 4,606,085 A | 8/1986 | Davies | 4/623 |
| 4,723,690 A | 2/1988 | vom Hofe | 221/96 |
| 4,752,020 A | 6/1988 | Grueter et al. | 222/402.15 |
| 4,769,863 A | 9/1988 | Tegg et al. | 4/625 |
| 4,776,494 A | 10/1988 | Holoubek | 222/207 |
| 4,784,652 A | 11/1988 | Wikstrom | 604/295 |
| 4,896,144 A | 1/1990 | Bogstad | 340/691 |
| 4,928,857 A | 5/1990 | Ecker | 222/211 |
| 4,946,070 A | 8/1990 | Albert et al. | 222/52 |
| 4,946,072 A | 8/1990 | Albert et al. | 222/105 |
| 4,994,265 A | 2/1991 | White | 424/73 |
| D315,196 S | 3/1991 | Tegg et al. | D23/284 |
| 5,105,992 A | 4/1992 | Fender et al. | 222/185 |
| 5,197,895 A | 3/1993 | Stupecky | 439/194 |
| 5,209,377 A | 5/1993 | Steiner et al. | 222/189 |
| D341,741 S | 11/1993 | Allen et al. | D6/542 |
| 5,287,996 A | 2/1994 | Uhlig | 222/189 |
| 5,307,953 A | 5/1994 | Regan | 222/82 |
| 5,335,855 A | 8/1994 | Borod | 239/152 |
| 5,377,874 A | 1/1995 | Brown | 222/82 |
| 5,398,848 A | 3/1995 | Padamsee | 222/94 |
| 5,405,269 A | 4/1995 | Stupecky | 439/191 |
| D359,868 S | 7/1995 | Brandenburg et al. | D6/545 |
| D371,514 S | 7/1996 | Daansen | D9/448 |
| D371,966 S | 7/1996 | Daansen | D9/448 |

(List continued on next page.)

OTHER PUBLICATIONS

HACCP Handwash Supervisor©, CFEI Conception Fabrication Electronique Industrielle, Place de la Halle, 89110 La Ferte Loupiere, France.
HyGenius Handwashing Verification—Compliance Control, Compliance Control© 1999.
The Clean Hands Company, Clean Hands Hand Washing Monitor, 10830 Galt Industrial Drive, St. Louis, MO 63132, © 1998 ShoeDesigns Multimedia.
Mobile Hand Washing Unit, H+P Labortechnik.
Wallgate, Recessed, Molded Hand Washer–Dryer, Chem–Plus Inc.

*Primary Examiner*—John A. Tweel
(74) *Attorney, Agent, or Firm*—Woodard, Emhardt, Naughton, Moriarty & McNett

(57) ABSTRACT

"Portable, individualized, hand washing agents dispensers are filled and checked out from a control station to healthcare workers and worn by the workers outside their clothing. Unique worker identification signature ID numbers in magnetic counterpart to bar code, and unique dispenser identification signature ID numbers in magnetic counterpart bar code are stored in computer memory. At patient treatment sites, infrared signal transmitters constantly producing a signal, differs at each site for a unique ID number identifying each site. An infrared signal receiver in a dispenser stores in on-board memory the site where the worker dispenses the hand wash agents. Upon return of a dispenser to the control station the amount of agents dispensed by the worker and time, date, and location are recorded. An alternative GPS site identifier is also described."

47 Claims, 3 Drawing Sheets

U.S. PATENT DOCUMENTS

| | | | |
|---|---|---|---|
| 5,573,041 A | 11/1996 | Skell et al. | 141/1 |
| D378,196 S | 2/1997 | Daansen | D9/448 |
| D383,673 S | 9/1997 | Daansen | D9/448 |
| D383,674 S | 9/1997 | Daansen | D9/448 |
| D383,675 S | 9/1997 | Daansen | D9/448 |
| D384,284 S | 9/1997 | Daansen | D9/448 |
| 5,683,012 A | 11/1997 | Villaveces | |
| 5,771,925 A | 6/1998 | Lewandowski | 137/552.7 |
| 5,801,735 A | 9/1998 | Lorenze, Jr. et al. | 347/29 |
| 5,810,201 A | 9/1998 | Besse et al. | 222/39 |
| 5,812,059 A | 9/1998 | Shaw et al. | 340/573 |
| 5,842,608 A | 12/1998 | Buchler | 222/181.3 |
| 5,945,910 A | 8/1999 | Gorra | 340/573.1 |
| 5,960,991 A | 10/1999 | Ophardt | 222/1 |
| 5,988,429 A | 11/1999 | Coe | 221/25 |
| 6,000,429 A | 12/1999 | Van Marcke | 137/624.11 |
| 6,038,331 A | 3/2000 | Johnson | 382/100 |
| 6,050,450 A | 4/2000 | Gardos | 222/1 |
| 6,053,604 A | 4/2000 | Sato et al. | 347/85 |
| 6,062,420 A | 5/2000 | Krouwel et al. | 221/5 |
| 6,070,958 A | 6/2000 | Kanome | 347/7 |

HAND WASHING COMPLIANCE MEASUREMENT AND RECORDING SYSTEM

BACKGROUND OF THE INVENTION

This invention relates generally to the field of healthcare, and more particularly to a method and combination for encouraging hand washing and for determining compliance with hand washing requirements in healthcare settings.

Tens of thousands of people die each year from infections they acquire while they were a patient in a hospital. These infections were unrelated to their initial hospital admission. A hospital acquired infection is called a "nosocomial infection."

The CDC (Center for Disease Control & Prevention) in the United States, has reported data that shows that more than 50% of all nosocomial infections can be directly related to the transmission of harmful bacteria by healthcare workers who have not properly washed their hands before and after each patient contact.

The number one reason given for healthcare workers not following proper hand washing guidelines is "not enough time and not enough conveniently located hand washing stations to wash hands as often as required."

The problem of insufficient hand washing is becoming worse. Hospitals through staff reductions are requiring healthcare workers to attend to more patients during the healthcare worker's work shift. Additionally, high transmission rates of antibiotic resistant bacteria and viruses require more adherence to the CDC hand washing guidelines. Hospital administrations are searching for products and services that encourage hand washing, and a means to ensure and measure compliance.

The problem of hand washing has been recognized for many years, and various efforts have been made to address it. Obviously, many types of devices and agents have been developed for assisting in the hand washing function. Another aspect of the matter is determining whether or not there has been compliance with hand washing directives. A recent U.S. Pat. No. 6,038,331, issued Mar. 14, 2000, discloses combination and a method for monitoring hand washing. Another is U.S. Pat. No. 5,945,910, issued Aug. 31, 1999 for a method and combination for monitoring and reporting hand washing. Another approach, although not measuring or checking for compliance, is directed to alerting someone of the need to wash their hands. This is addressed in U.S. Pat. No. 4,896,144, issued Jan. 23, 1990 for a hand washing alert. Another patent directed to a method and system for improving hand cleanliness, primarily in a food service environment, is U.S. Pat. No. 5,812,059, issued Sep. 22, 1998. It discloses a method and system for improving hand cleanliness. In this one, an indicator worn by a worker, is activated when the worker leaves a food handling area. The indicator, worn by the worker, is deactivated by a deactivating device associated with a hand cleaning station, and only when it is determined that the worker has used the hand cleaning station before re-entry to the food handling area. The above-mentioned patents are the closest of which I am aware dealing with the matter of monitoring hand washing.

There are some products which have been advertised in connection with monitoring hand washing. A so-called "HACCP" Hand Wash Supervisor, marketed by CFEI at Plas de la Halle, 8910 La Ferte Loupiere, France. Another organization marketing with the brand "HyGenius" advertises "Over 10,000,000 perfect hand washes." Another monitoring combination is offered by The Clean Hands Company of 10830 Galt Industrial Drive, St. Louis, Mo. 63132. In this system, according to the marketing information, each employee wears an ID badge. A detector at each entrance of a restroom will notify a central computer system when an employee enters, and will wait for the employee to wash their hands before leaving. The employee applies the proper amount of soap, rubs hands together to generate the appropriate lather, and places hands under the camera eye of the instrument in the restroom which, in 5 seconds, will analyze and reveal a "pass" or "fail" reading. An employee can add soap if needed and retest as many times as necessary to pass. Once a "pass" has been achieved, the soap can be rinsed. The "pass/fail" information is fed to a central computer, whereby the employer can determine whether or not an employee is cooperating. Their "web" address is http:H/www.cleanhandsco.com.

The foregoing prior art systems appear to focus on the use of soap, water and sink basins for hand washing. While that is the conventional approach to hand washing, it has been found that, in many circumstances, there is no visually observable evidence of soil on the hands, so they appear clean and not in need of hand washing. In such cases, it may appear that there is no need for hand washing when, in fact, the hands may be seriously contaminated with transient bacteria and/or viruses. Besides, soap and water and a sink are not always conveniently located relative to the treatment site for a patient. In an effort to address this problem, antimicrobial products have been developed and marketed in containers or packages that can be carried by the healthcare worker. These contain an alcohol-based waterless and fast drying gel which can be dispensed on the hands before and after each patient contact, at the patient contact location. But, to my knowledge, there has not been a way to reliably monitor usage of such dispensing containers or packages.

While the foregoing comments have been directed to the hospital environment, it can be understood easily that they apply also to other healthcare institutions of various sizes from clinics, down to doctor's offices, down to kiosks, or temporary set-ups in shopping malls for tasks as simple as shots for influenza or cholesterol screenings. While these latter situations might not currently fall under any regulatory organizations' hand washing protocols or compliance requirements, a much larger area is also envisioned. An example is in the case of dealing with disasters, epidemics or other circumstances in which large outdoor areas are dedicated, at least on a temporary basis, to treatment of patients. For certain types of treatment, it may be just as important that hand washing be done as it is in a hospital setting. Moreover, it may be important to monitor compliance on a real-time basis.

The present invention is directed to addressing the problems heretofore involved in connection with encouragement of hand washing, and monitoring compliance with hand washing directives.

SUMMARY OF THE INVENTION

Described briefly, according to one embodiment of the present invention, portable, individualized, filled hand washing agents dispensers are provided from a control station to healthcare workers. Unique worker identification "tag" (ID#), and unique dispenser identification "tag" (ID#) are stored in computer memory. At patient treatment sites of a healthcare facility, wireless signal transmitters are employed, constantly producing a wireless signal. Each dispenser includes a wireless signal receiver, an agents dispensing actuator and information storage device. The receiver is responsive to reception of wireless signals to insert into the storage device, an event signal. When the worker dispenses the hand wash agents, it is recorded in the storage device to represent a hand washing event. The dispenser is worn externally on the health care worker during the entire work shift. At the end of the shift, the dispenser is returned to the control station which has means to identify the dispenser and determine the amount and type of agents dispensed during the work shift, and store that information for subsequent tabulation and reporting. The control station also relates the unique identification signature tag of the dispenser to the unique identification tag of the worker and the amount and type of agents used and stores that information, as well as the unique transmitter site, date and time information from the event record in the dispenser storage, thus tracking the time, date and location, of each occasion specified for use of the dispenser and whether or not the worker dispensed agents from the worker's assigned dispenser, during the work shift.

According to another embodiment of the present invention, the hand washing agents dispensers also include a radio transmitter capable of transmitting to a satellite component of a global positioning system. The transmitter transmits, on a real-time basis, information from the dispenser identifying the dispenser, the date and time when a dispensing event takes place, and the global positioning system identifies the location of the dispenser when the transmission is made. That information can be monitored on a real-time basis or stored in a management computer for access and use by management to deal promptly, if desired, with any sensed failure or inadequacy of hand washing events associated with a particular dispenser and, thereby, by the healthcare worker to whom the dispenser has been checked out.

DESCRIPTION OF THE ILLUSTRATED EMBODIMENT

Figure 1:
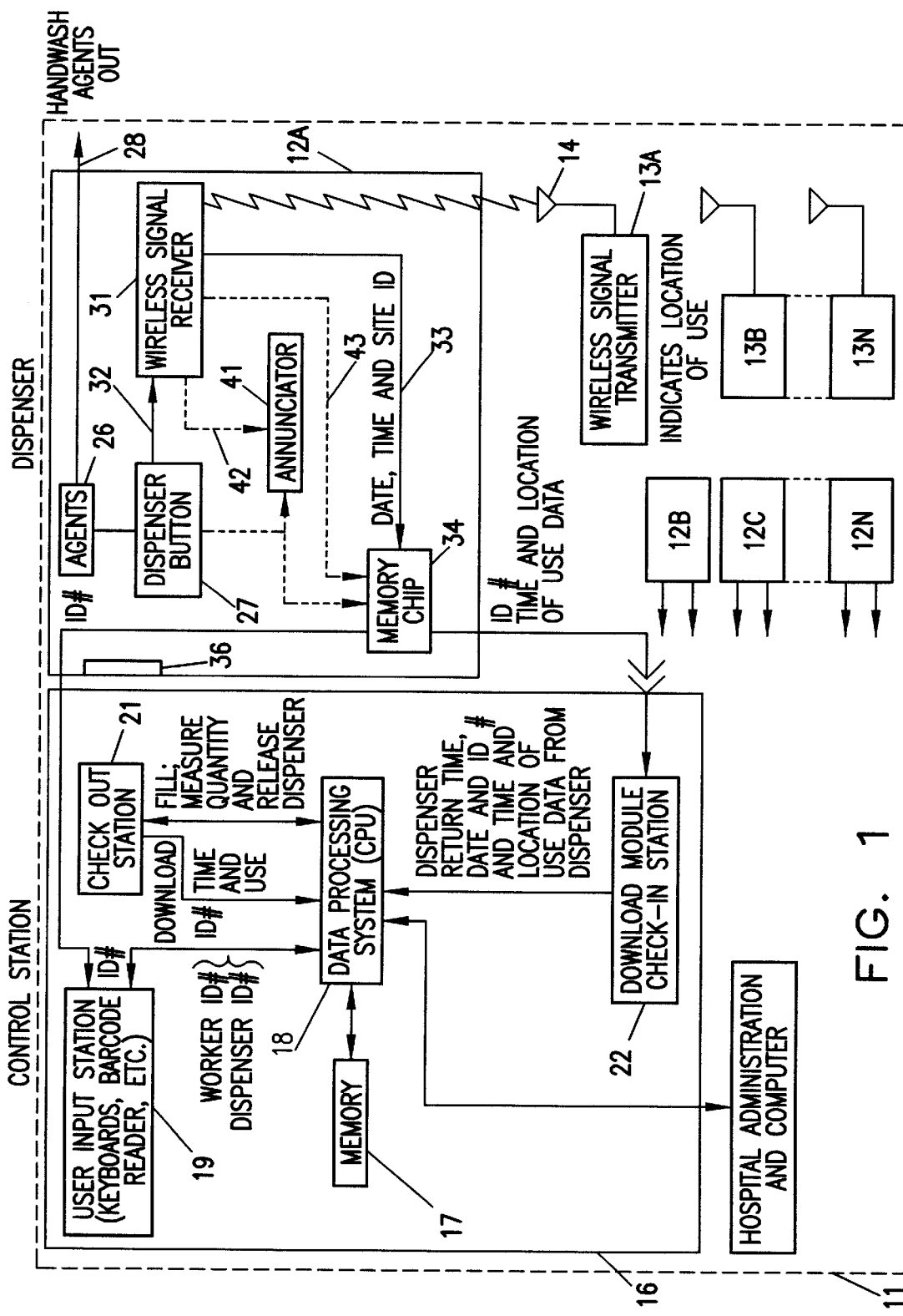
FIG. 1 is a block diagram of an inventive system according to one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1 of the drawing, the dashed outline represents a healthcare facility 11. There is a plurality of hand washing agents dispensers 12 used in that facility. One of them is shown in the large block 12A and the rest are designated in the smaller blocks 12B through 12N. Each of the dispensers has its own individual identifier "tag" different from each of the others. Such tag can be, for example, but without limitation, a human readable numerical or alpha-numerical identifier tag, or a bar code tag on the outside of the dispenser and a corresponding identifier tag stored in memory in the dispenser. Also, there is a set of wireless signal transmitters 13, designated in blocks 13A through 13N located at various patient diagnosis and treatment sites in the facility. Each of the transmitters 13A through 13N is identical to each of the others except that each produces a wireless signal that is unique and different from the wireless signal produced by each of the others. The wireless nature is represented by the antenna 14 and may be of any of a variety of natures from ultrasonic through radio, "blue tooth" and light frequencies, for example, but infrared is considered the preferred choice at the moment. Electrical supply to the transmitters may be the electrical system of the healthcare facility, with battery back-up in each of the transmitters.

The facility 11 also includes one or more control stations 16 depending upon the size of the facility. For purposes of present example, and to facilitate description, only one is shown. It includes computer memory 17, a central processing unit 18, a user input station 19, a check-out station 21, and a check-in station 22.

In the dispensers, there is a supply 26 of hand wash agents and operable by a dispenser button 27 to dispense a predetermined amount (one dose) per button actuation and which is discharged from the dispenser 28. Two examples of supply 26 are a carousel of single dose cartridges or a multidose reservoir. There is a wireless signal receiver 31 capable of receiving the wireless signals transmitted by any of the transmitters 13. In addition to dispensing agents from supply 26, the button 27, when pressed, being coupled to the wireless receiver as designated by line 32, enables the wireless signal receiver to receive a signal from any of the transmitters 13. Upon receiving such signal, the wireless signal receiver transmits that information event on line 33 to memory 34 for storage of the date, time and identification of the site from which the transmitter signal was received, based upon the particular identifying signature in the signal from the transmitter. The memory 34 also stores the identification of the dispenser itself. In addition, there may be an identification strip or other indicia 36 on the dispenser itself, if that is preferred over direct identification from the memory 34, for some particular application.

Having described the general organization of components, a method of operation according to the present invention will now be described.

A healthcare worker inputs data at the user input station 19. The preferred procedure is for the worker to enter his or her own personal identification information. This can be done by the use of a keyboard or by use of a bar code on an identification badge or some other unique code device worn on or embedded in the person, or by fingerprint. Other types of identifier input may also be used. Once the personal identifier has been entered, the worker may enter the type of hand wash agents to be used in the dispenser to be checked out to the worker. This information is delivered to the processing unit 18, stored in memory 17, and transmitted to the check-out station 21. The dispenser 12A at the delivery point of the check-out station is then filled with the appropriate hand wash agents, its identification is read from the memory 34 and/or from an external identifier 36, transmitted to the processor 18 and to memory 17. The quantity of agents required to fill the dispenser is measured and transmitted to the processor 18 and stored in memory 17 along with the identification of the last prior user of the particular dispenser. In this way, the amount of agents used during a shift by the worker who last used the dispenser, is made of record in memory 17.

As the worker removes the dispenser from the check-out station, the worker immediately attaches the dispenser to his/her clothing and/or body outside the clothing in plain sight for the duration of the work shift. Attachment can be a variety of ways. Hook or spring clip are a couple of examples. Then the worker begins making rounds.

When the worker arrives at a patient treatment site, hand washing is expected before contact with the patient. To do this, the worker, holding the dispenser in the palm of one hand, places the dispenser in position to dispense a dose of agents as at outlet 28 in FIG. 1, onto the other hand and pushes a button or other dispensing actuator 27 with the dispenser holding hand. This dispenser delivers a pre-set dosage amount of hand wash agents from storage 26 in the dispenser. At the same time, it activates through line 32, the wireless signal receiver 31, which then is enabled to receive a signal from transmitter 13A and which has a character unique to that particular transmitter at that treatment site. The signal receiver 31 transmits information regarding the identification of the treatment site, the date, and time of actuation, along line 33 to memory 34 in the dispenser. That information is stored in memory 34 along with the identification of that particular dispenser which always is stored and available from that memory 34.

Then the healthcare worker moves on to the next patient treatment site. Such treatment sites can be as near as one bed is to another in a hospital room. But it would have its own separate wireless signal transmitter, such as 13B, for example.

Again, the worker is expected to wash hands before contact with the patient at the second treatment site. Upon actuating the dispenser actuator 27, agents is dispensed onto one hand of the worker and the wireless signal receiver is enabled to receive a signal from the transmitter 13B. The receiver then transmits the identification site of transmitter 13B, the date and time to the memory 34 where that information is stored. This procedure continues as the worker makes the rounds of the healthcare facility.

Figure 3:
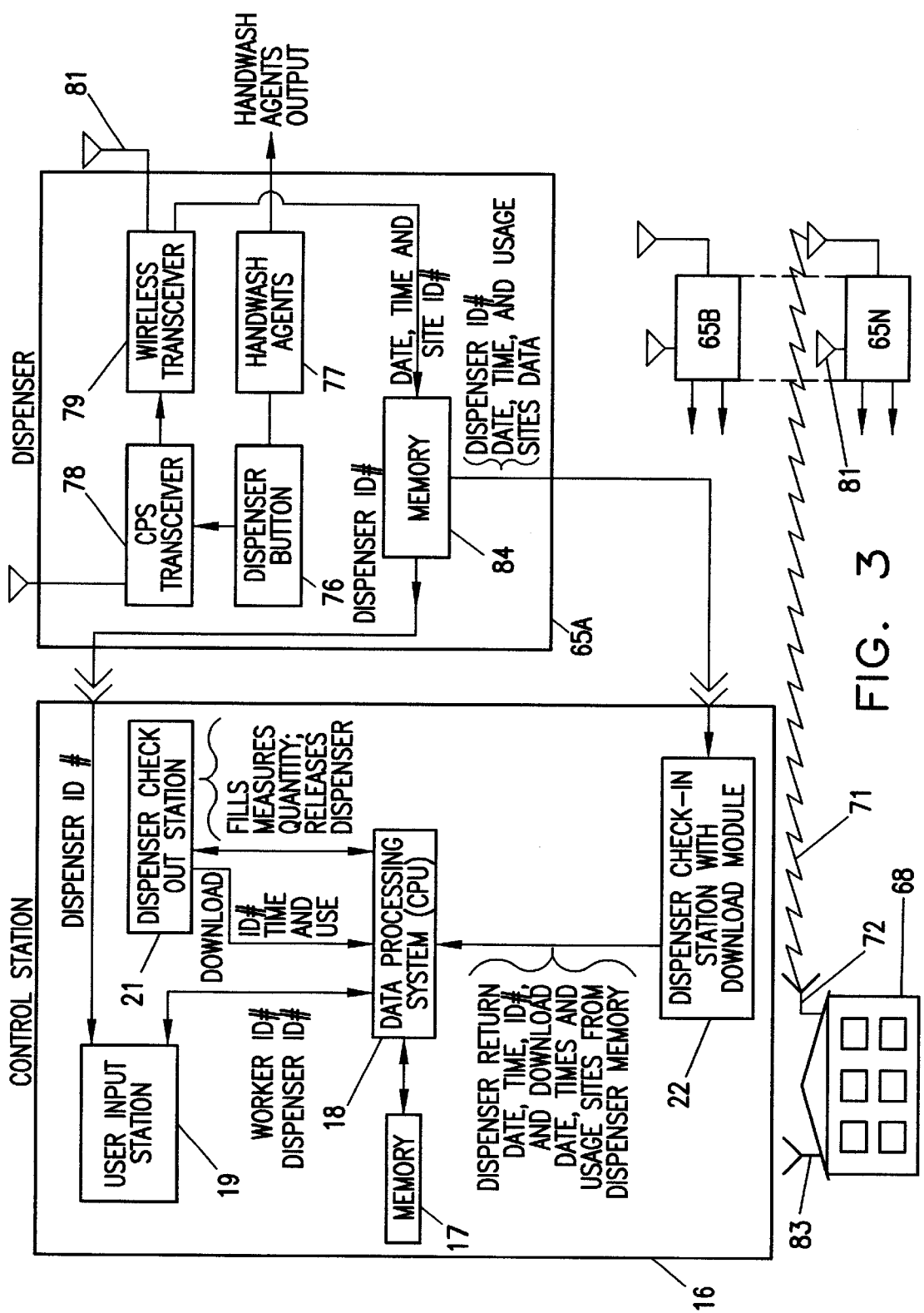
FIG. 3 is a block diagram of the system according to the embodiment shown in FIG. 2.

At the end of a shift, the worker returns to the control station and delivers the dispenser into a slot at the check-in station 22. Upon reception in the check-in station, a tag reader records the dispenser's unique identification, and the station records the return date and time, and downloads by way of wireless transmission or direct data port connection, that information along with the dispenser's use data collected in dispenser during the worker's work shift, through the data processing unit 18 to memory 17. The dispenser remains in the control station along with other dispensers returned by other workers, to eventually be re-filled with agents and checked out. Although the FIGS. 1 and 3 block diagrams position the check-out station above the check-in station, the check-in station will be physically above the check-out station, so dispensers returned to the slot in the check-in station will be at the top of a stack, and moved downwardly in the stack as other dispensers are checked out at the bottom of the stack. When this particular dispenser has advanced downwardly to the point where it is in position to be checked out and, after the next worker to use it has entered the required information to enable check-out, this dispenser is filled with the designated hand washing agents. During or following the fill, the amount of agents required to fill it, is measured. That information is transmitted to the data processing unit 18, matched with information stored in memory 17 from the prior user, and stored in memory. In this way, a record is made of the amount of hand washing agents dispensed by a healthcare worker who used this dispenser during a prior work shift. At the same time, this particular dispenser is ready for check-out by the next healthcare worker to use it. Alternatively or additionally, downloading of a dispenser's use data during a given prior user worker's work shift can also be executed at the time the dispenser is being re-filled prior to being checked-out for the next user or the next shift of the prior user. This can be done at the check-out station as indicated in FIGS. 1 and 3 between blocks 18 and 21.

The foregoing sequence of events enables the administration of the healthcare facility to determine the compliance of a healthcare worker with the facility's requirements pertaining to hand washing activity. Of course, the facility administrators can also enter into memory, patient records, compliance procedures and specifications, and have the control station compare a healthcare worker's record with requirements, and produce an output record of worker compliance. If desired, data storage, comparison, charting and the like can be accomplished at some location in or outside the control station or healthcare facility, if desired. It is thought that the preferred arrangement in terms of number and location of control stations, depends upon the size and organization of the healthcare facility for optimum accessibility to workers for check-in and check-out functions at the beginning and end of work shifts. The attaching of the dispenser to the worker in a way that it is clearly and always in sight, and convenient to use, rather than in a pocket, encourages the timely use of it.

One alternate arrangement to further encourage the healthcare worker to wash hands in a timely fashion, is indicated by some dashed lines in the dispenser 12A shown in FIG. 1. According to this method, when the healthcare worker reaches a patient treatment site such as adjacent a hospital bed, for example, the wireless signal receiver responds to the signal transmitter such as 13A and does two things. First of all, it signals the annunciator 41 as indicated along dashed data line 42 and turns it on. This annunciator can be a flashing light or a vibrator or an audible signaler in the dispenser itself. Secondly, the receiver also signals along line 43, the memory 34 to make a record of the date, time and site that the worker entered. Then, upon operation of the dispenser actuator such as 27, it would turn off the annunciator 41 and signal the memory 34 that the dispensing event has occurred. It will be recognized that, in this case, the wireless signal receiver 31 is enabled at all times to receive a signal from any of the transmitters, instead of being turned on only upon activation of the dispenser actuator 27, as in the previously described embodiment. Thus the receiver sets the annunciator to "on," and the dispenser actuator resets it to "off". However, if the worker fails to use the dispenser actuator 27 in response to annunciation, then the annunciator is terminated by automatic reset within short duration (5–10 seconds, for example) but the fact would still be recorded into memory that a hand washing event was signalled but not executed. Another example of a reset scheme could be that, if the worker fails to use the dispenser at the one site, the annunciator will be automatically and momentarily reset by reception of a wireless signal from the transmitter at the next site visited. Also, as above, the failure of the worker to wash hands at the previous site will be recorded in the dispenser memory. After the momentary reset to "off", the annunciator is set to "on" at the said next site, to alert the user to wash hands.

More often than not, the hand washing agents will be an antimicrobial fluid. But it may be other types and forms of agents. Powders or gels are a couple of examples. They may be dispensed as a stream, mist, cloud or, more likely, a spray. Reports can be generated from the data processing system which will provide the following compliance information:

1) Healthcare worker ID#;
2) Fluid dispenser ID#;
3) Fluid used ID# (type of fluid);
4) Where in location (site) was fluid dispenser used;
5) Time, date fluid dispenser was used at a given location (site);

6) Time, date fluid dispenser was checked-out from control station;
7) Time, date fluid dispenser was returned to control station;
8) Patient contacts during fluid dispenser's use by healthcare worker;
9) Total number of dose applications from fluid dispenser during a given time.
10) Time, date and location sites where hand washing events were signaled for but were not performed.

Hospital administrations will differ in the amount of information they require for compliance reporting relating to healthcare worker hand washing. Some hospitals will only require information regarding:

1) How many hand washes a healthcare worker performed during a given work shift; and
2) What fluid dispenser by ID is issued to a healthcare worker at a given time, on a given date.

Some hospitals will issue fluid dispensers to: patients, tech staff, maintenance personnel, administrative personnel, etc., without requirements to measure compliance. In such applications a disposable fluid dispenser would be utilized and the control station will have the primary function of being a delivery device. If a compliance report relating to who used what disposable fluid dispenser on what date/time and how many dose applications were dispensed, then the control stations would record such information. The amount of fluid used would be measured also at the control station by means of weight, optics or electronics, based on the differential readings of the disposable fluid dispenser at the time of delivery to the user and at the time of return upon completion of its use. For a disposable dispenser, the simple procedure would be to weigh the full one before or upon check-out, and weigh it again upon check-in at the check-in station.

Figure 2:
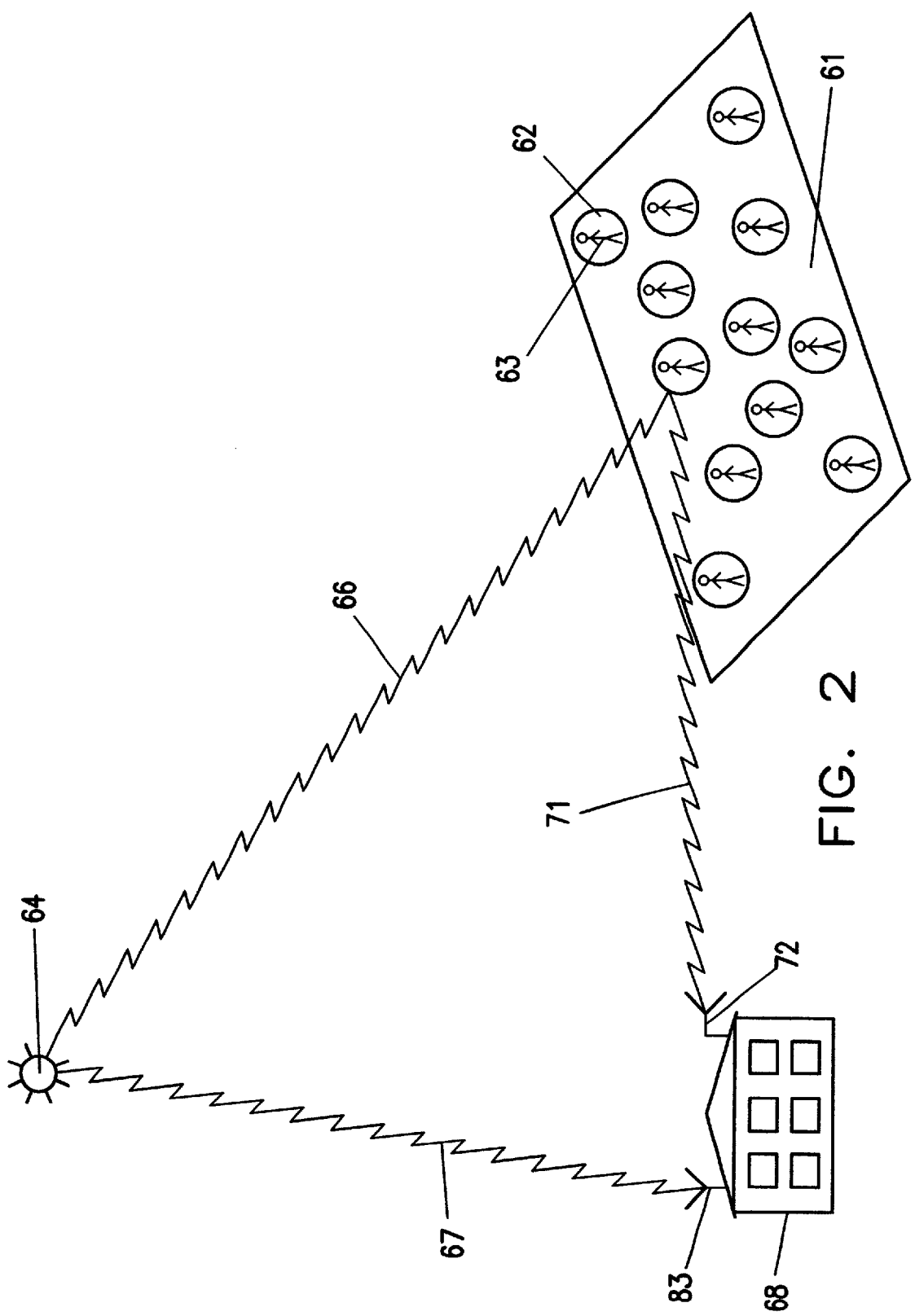
FIG. 2 is a block diagram of the system according to another embodiment of the present invention.

It was mentioned above, that hand washing and the importance thereof are not limited to individual healthcare facilities. Occasions arise when delivery of healthcare is inside or outside any temporary or permanent building site and where facilities including sinks, water, and antimicrobial supplies are not readily available. Examples are disasters where many people are injured, or there are mass inoculations to address diseases or anticipated outbreaks of disease. FIG. 2 represents schematically, one possible scenario for large scale inoculation against or treatment for epidemic disease. In this example, a soccer field 61, is reserved for numerous patient treatment stations 62 at which at least one healthcare provider 63 is stationed for treatment of numerous patients. Even though many sick or persons at risk will be treated in each station, it is important that hands be washed between the event of treatment of one patient and that of another. Also, it is desirable that tracking of hand washing events be maintained and, in this instance, on a real-time basis.

To avoid the necessity of a permanent establishment and the time required to set up transmitters at individual stations as has been described in the previously described embodiments, in this instance, a geosynchronous satellite 64 is employed in orbit. This satellite is used as the hub of a global positioning system. As in the previously described embodiment, each of the healthcare workers has an antimicrobial dispenser much like that in the previously described embodiment. In this instance, however, instead of or in addition to the infrared receiver, it has a radio transmitter communicating with the satellite 64 which, upon receipt of a signal from the transmitter as indicated schematically along the wireless signal line 66, responds with the rather precise geographical location of the station from which the signal has been transmitted. The location identification response may be transmitted from the satellite to a monitoring station as indicated along the wireless signal path 67 from the satellite to the monitoring station 68 where the identification of the dispenser and its location information are received in the monitoring station 68, each time a dispensing event occurs. In that way, persons monitoring the activity can be aware on a real-time basis of the dispensing of hand washing agents at each station. Of course, the information can be stored as well in a computer at the monitoring station 68. Because many satellites are used for a variety of functions, and there are space limitations in them, an alternative arrangement would provide for the dispenser to also have a wireless communication path along line 71 from a cellular or other radio transmitter in the dispenser to a corresponding receiver 72 at the monitoring station 68. Accordingly, reception on a real-time basis, and storage for future use, of information identifying the dispenser, the time, date, and place of use at each hand washing agent dispensing event, is available using the global positioning system for location of the event. It will be recognized that this embodiment of the invention provides a capability of monitoring activity in a fairly large geographical area not confined to a single building or a single set of buildings in one geographical location. The dispenser check-out and check-in procedure is essentially the same as described above for the first embodiment, and information regarding location as transmitted to the dispenser from the satellite, is stored in memory in the dispenser so that, if and as the health care worker moves from station-to-station, that information will be stored in the dispenser itself, as well as being stored in a computer at the administration building 68.

Referring now to FIG. 3, the block diagram there shows in more detail than FIG. 2, the dispenser component and central station component of that embodiment of the invention. Each of the dispensers 65A through 65N is similar in many respects to that shown for the first embodiment of the invention. More specifically, it is provided with a clip or other suitable means for attachment to the outside of the healthcare worker. Also, it has a dispenser button 76 operable when actuated to discharge a dose of hand wash agents from the supply 77 into a hand of the user. It also actuates the global positioning system (GPS) transceiver 78 to query the satellite 64 (FIG. 2) as to its location. It receives the response from the satellite and, translating at either the satellite or more likely in the transceiver unit 78, translates the site location to a wireless transceiver 79 for transmitting that information from antenna 81 directly to antenna 72 at the administration building 68. An alternative possibility, if the satellite has the capability to do so, is that it can transmit the site location information directly on the path 67 to antenna 83 at building 68. Transmission between antennas 81 and 72 can be any of a variety of communication channels, wireless telephone of the cellular or other type being just one possibility. In addition to the site location information determined through GPS, the transceiver 79 also transmits the information regarding date, time and the site identification number to the administration building. The transceiver also provides that information to the memory 84 in the dispenser for subsequent downloading into the check-in station 22 of the control station 16. Thus, it can be seen that the control station 16 may be essentially identical to that in the previously described embodiment, whereas the dispensers are somewhat different to adapt them to the global positioning system environment and real-time transmission of all of the same information to the administration building as it is being stored in memory 84.

It can be recognized that this embodiment of the present invention can be used over a much larger area than within the confines of a hospital. It can be used where a healthcare provider travels by golf cart or bicycle or other transportation means from site-to-site, particularly where, in addition to providers who are stationed at particular sites, a specialist or supervisory provider moves from site-to-site continuously.

Having thus described the organization of components, and the method of operation, it can be recognized that there are devices currently known in the art and available for assembling an organization according to this description and within the skill of the art. Therefore, while three embodiments of the invention have been illustrated and described in detail in the drawings and foregoing description, the same is to be considered as illustrative and not restrictive in character, it being understood that only representative embodiments have been shown and described and that all changes and modifications that come within the spirit of the invention are desired to be protected.

What is claimed is:

1. A method for monitoring hand washing agents dispenser activity and comprising:
   entering into computer memory, for certain users of a care facility, a personal identifier unique for each user; and
   providing hand washing agents dispensers with individual dispenser identification tags unique to each dispenser, and entering into computer memory, said dispenser identification tags.

2. The method of claim 1 wherein:
   time and date data is entered into said computer memory at correlating times the computer memory receives said user identifier and said dispenser identifier tag.

3. The method of claim 1 further comprising:
   recording into computer memory by its unique identifier tag, what dispenser is issued for use to what user by that user's unique identifier.

4. The method of claim 1 further comprising:
   recording into computer memory by a dispenser's unique identifier tag, what dispenser is returned after usage, along with the user's unique identifier.

5. The method of claim 1 and further comprising:
   recording into computer memory, the quantity of individual doses of hand washing agents that are contained within a dispenser by using the dispenser's unique identifier tag prior to issuance to a user, and recording simultaneously into said computer memory upon issuance of the dispenser to the user, the user's unique identifier.

6. The method of claim 5 and further comprising:
   recording into computer memory, the amount of individual doses of hand washing agents dispensed by a dispenser by using its unique identifier code, upon its return by a user identified by the user identifier, at the end of its designated time usage.

7. The method of claim 1 and further comprising:
   issuing to a person titled as a user having a unique personal identification tag, one of said hand cleaning agents dispensers specifically for use to monitor that person's use activity of said one dispenser.

8. The method of claim 1 and further comprising the step of preparing a report providing the following information:
   A) user ID#;
   B) hand washing agents dispenser ID#;
   C) hand washing agents dispensed by dispenser;
   D) dispenser issuance date, time;
   E) dispenser return date, time;
   F) total number of dose applications dispensed by dispenser during its time of a given usage duration by user.

9. The method of claim 8 and further comprising:
   entering into computer memory, standards for healthcare worker hand washing; and
   comparing said report information with said standards.

10. The method of claim 1 where the users are healthcare workers, the method further comprising:
    filling said dispensers with predetermined amounts of hand washing agents;
    checking out filled dispensers to said workers; and
    recording for each of said workers, the identification of which of said dispensers is checked out to said worker.

11. A method according to claim 10 and further comprising:
    checking out filled dispensers to said workers;
    recording for each of said workers, the identification of which of said dispensers is checked out to said worker; and
    transmitting wireless signals at patient treatment sites, the signals at different sites being different for identification of and distinguishing between sites.

12. A method according to claim 11 and further comprising:
    dispensing some of said agents from a first of said dispensers at a first treatment site;
    receiving in said first dispenser, the said wireless signal at said first site; and
    entering data into memory in said first dispenser in response to receipt of said wireless signal from said first site.

13. The method of claim 12 and wherein:
    said receiving step is initiated by said dispensing step.

14. The method of claim 12 and further comprising:
    dispensing some of said agents from said first dispenser at a second treatment site;
    receiving in said first dispenser, the wireless signal at said second site; and
    entering data into memory in said first dispenser in response to receipt of said wireless signal from said second site.

15. The method of claim 12 and further comprising:
    dispensing some of said agents from a second of said dispensers at said first treatment site;
    receiving in said second dispenser, the said wireless signal at said first site; and
    entering data into memory in said second dispenser in response to receipt of said wireless signal from said first site.

16. The method of claim 12 and wherein:
    the data entering step includes entry of the date, time and site of the dispensing step.

17. The method of claim 12 and further comprising steps for:
    refilling the first dispenser; and
    measuring the amount of hand washing agents used in refilling the first dispenser.

18. The method of claim 17 and further comprising:
    checking-in said first dispenser; and
    storing in computer memory, the refilling amount measured and the identification of the first dispenser, along with identification of the worker who last checked in said first dispenser.

19. The method of claim 12 and further comprising:
wearing said first dispenser by said worker in full view following check-out, and holding said first dispenser in the palm of one hand by the worker while dispensing said agents from said dispenser.

20. The method of claim 12 and further comprising:
causing reception in said first dispenser, of the wireless signal at said first site, to activate an annunciator on said first dispenser.

21. The method of claim 20 and further comprising:
causing the step of dispensing some agents at said site, to de-activate said annunciator.

22. The method of claim 12 and further comprising:
checking-in said first dispenser and downloading data from said dispenser memory in said first dispenser into computer memory separate from said first dispenser.

23. The method of claim 15 and further comprising:
checking-in said dispensers after use;
downloading event data records from memories in said checked-in dispensers into computer memory separate from said dispensers in response to check-in of said dispensers; and
relating the check-in data from each dispenser to the check-out data for the dispenser.

24. The method of claim 23 and further comprising the steps of:
entering into computer memory, standards for health care worker hand washing; and
comparing said event data records with said standards.

25. The method of claim 23 and further comprising:
preparing a report providing the following information:
a) Healthcare worker ID#;
b) Fluid dispenser ID#;
c) Fluid used ID# (type of fluid);
d) Where in location (site) was fluid dispenser used;
e) Time, date fluid dispenser was used at a given location (site);
f) Time, date fluid dispenser was checked-out from a control station;
g) Time, date fluid dispenser was checked in to a control station;
h) Patient contacts during fluid dispenser's use by healthcare worker;
i) Total number of dose applications from fluid dispenser during a given worker's work shift time;
j) Time, date and location sites where hand washing events were signaled for but were not performed.

26. The method of claim 10 and further comprising:
establishing patient treatment sites;
dispensing hand washing agents from said dispensers at said sites;
communicating between individual ones of said dispensers with a global positioning system satellite upon the dispensing of antimicrobial agents from one of said dispensers; and
transmitting in response to the dispensing step, the site location and time information to storage.

27. The method of claim 26 and further comprising:
transmitting said location and time information in real time to a monitoring station.

28. In a system for monitoring hand washing activity, the combination comprising:
a plurality of treatment sites;
data collection and storage apparatus including a computer memory;
means for producing wireless signals identifying site locations;
a plurality of worker identifiers in computer memory, each identifier being unique for identifying a particular worker; and
a plurality of hand wash agents dispensers, each dispenser having a unique identifier identifying that dispenser, and each dispenser storing hand washing agents, and each dispenser having a wireless signal receiver responsive to location identifying signals from said wireless signal producing means, and each dispenser having a memory, and each dispenser having an agents dispensing actuator operable, when actuated, to cause a dispensing event to dispense hand wash agents from said dispenser.

29. The combination of claim 28 and further comprising:
a dispenser check-in station operable with said dispensers to recognize the identities of said dispensers and to read data stored in said dispenser memories, and to record stored data with dispenser identification;
a worker identifier recognition device cooperable with the worker identifier and the dispenser identifier and the check-in station to relate check-in data to the worker in the record; and
agents measuring means operable with said dispensers to measure the quantity of said hand washing agents in the dispensers individually.

30. The combination of claim 28 and wherein:
said dispensers are portable, sized to be held in a hand, with the actuator operable by a part of the holding hand.

31. The combination of claim 28 and wherein:
each dispenser has an annunciator activated in response to said receiver receiving a wireless signal from said means for producing wireless signals, and de-activated in response to actuation of said agents dispensing actuator.

32. The combination of claim 28 and wherein:
the dispenser memories are electronic storage devices.

33. The combination of claim 28 and wherein:
said means for producing wireless signals comprise a geosynchronous global positioning system satellite.

34. The combination of claim 28 and wherein:
said means for producing wireless signals are infrared transmitters; and
said receivers are infrared signal receivers.

35. The combination of claim 34 and wherein:
said signal receiver of each dispenser is arranged to be enabled to receive signals from any of said transmitters, by operation of said agents dispensing actuator.

36. The combination of claim 28 wherein:
each of said dispenser memories stores dispensing event data indicating time, date, and site of a dispensing event.

37. The combination of claim 36 wherein:
each of said dispenser memories stores a dispenser identifier for said dispenser.

38. The combination of claim 36 wherein:
said dispensers are adapted to attachment to a health care worker and display outside the worker's clothes.

39. The combination of claim 28 and further comprising:
a user input station for receiving worker identifier input; and
a dispenser check-out station coupled to said user input station for enabling health care workers to check-out said dispensers.

40. The combination of claim 39 and wherein:
said check-out station includes a dispenser filler to fill said dispensers individually with hand wash agents.

41. The combination of claim 40 and wherein:

said check-out station is coupled to said user input station to enable said filler to fill a dispenser upon recognition of worker identification, and fill with agents specified by the identified worker, and store in said computer memory, information identifying the worker, the dispenser, the specified fill agents, the amount filled, the identification of the previous user of the dispenser, and the time and date of check-out of the dispenser to the present using worker.

42. An combination for monitoring hand washing activity, and measuring compliance with standards comprising:

computer memory storing a roster of workers of a health care facility and personal identification data for each worker;

hand washing agents;

portable hand washing agents dispensers, each having an individual identification tag, said dispensers being adapted to attach to said worker or worker's clothing and be worn outside the worker's clothing and containing said hand washing agents;

a check-out device coupled to said computer memory and storing said dispenser identification, for checking out said dispensers to said workers and recording for each of said workers, the identification of which of said dispensers is checked out to which of said workers;

a plurality of patient treatment sites;

a plurality of wireless signal transmitters, the transmitter at each patient treatment site transmitting a signal unique to the location of said transmitter;

a wireless signal receiver on each said dispenser for receiving said signals from said wireless signal transmitters;

a set and reset device on each dispenser and coupled to said receiver and set in response to any of said wireless signals;

a reset operator on each dispenser and coupled to said set and reset device, to reset said device when said dispenser is used to dispense said agents;

and an information storage device on each said dispenser and coupled to said receiver to store times, dates, and locations of set events and reset events.

43. The combination of claim 42 and wherein:

said computer memory stores a hand washing guideline database;

said hand washing agents comprise a fluid or gel containing antimicrobial constituents.

said portable hand washing agents dispenser is a fluid dispenser;

said reset operator is a fluid dispensing actuator;

said set and reset device is switched "on" when said receiver receives said wireless signal, and is switched "off" when said dispensing actuator used;

the combination further comprising:

a device which receives said fluid dispenser after use and which refills the fluid dispenser with hand washing agents and measures the amount of hand washing agents used by the prior using worker;

a device which downloads the information stored in the information storage device in the fluid dispenser; and a computer which compiles a database comprised of the worker identifier, the fluid dispenser identification tag, the times and dates the worker checked out and returned the fluid dispenser, the locations and times and dates when the fluid dispenser was used, and the amount of fluid used.

44. The method of claim 1 and further comprising:

wearing said dispensers by said users in full view, and holding one of said dispensers in the palm of one hand by a user while dispensing agents from said one dispenser.

45. The method of claim 4 and using disposable dispensers of known weight containing hand washing agents, and weighing the dispensers when returned after usage to determined the weight of agents dispensed.

46. The method of claim 4 and downloading dispenser usage information at a dispenser check-out station.

47. The method of claim 23 and further comprising:

checking in the dispensers at a check-in station located above a check-out station, and enabling the dispenser travel from said check-in station to a check-out station in a downwardly movement.

* * * * *